United States Patent
Schmitz

(10) Patent No.: US 6,544,375 B1
(45) Date of Patent: Apr. 8, 2003

(54) PROCESS FOR APPLYING DISCRETE WEB PORTIONS TO A RECEIVING WEB

(75) Inventor: Christoph Johann Schmitz, Euskirchen-Stotzheim (DE)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/831,780
(22) PCT Filed: Nov. 17, 1998
(86) PCT No.: PCT/US99/27228
§ 371 (c)(1), (2), (4) Date: May 14, 2001
(87) PCT Pub. No.: WO00/30583
PCT Pub. Date: Jun. 2, 2000

(30) Foreign Application Priority Data

Nov. 23, 1998 (EP) .............................................. 98122228

(51) Int. Cl.⁷ .......................... B32B 31/18; B32B 35/00
(52) U.S. Cl. ...................... 156/265; 156/264; 156/302; 156/519; 156/552
(58) Field of Search ................................. 156/256, 263, 156/264, 265, 269, 270, 516, 517, 519, 543, 556, 558, 552; 83/39, 42, 44, 408

(56) References Cited

U.S. PATENT DOCUMENTS

| 3,957,570 A | * | 5/1976 | Helm ........................ 156/519 |
|---|---|---|---|
| 4,767,487 A | | 8/1988 | Tomsovic, Jr. |
| 5,660,657 A | | 8/1997 | Rajala et al. |
| 5,759,340 A | | 6/1998 | Boothe et al. |
| 6,092,802 A | * | 7/2000 | Lackner et al. ............. 271/225 |

FOREIGN PATENT DOCUMENTS

| DE | 3431910 A1 | 3/1986 |
|---|---|---|
| EP | 0 304 044 A1 | 2/1989 |

OTHER PUBLICATIONS

PCT International Search Report for PCT/US99/27228, date of mailing: Mar. 7, 2000.

* cited by examiner

Primary Examiner—Richard Crispino
Assistant Examiner—Cheryl N. Hawkins
(74) Attorney, Agent, or Firm—Michael S. Kolodesh; Jay A. Krebs; Ken K. Patel

(57) ABSTRACT

The invention provides a process comprising the steps of: feeding a web into a web transfer apparatus (1) at a first speed (V1); cutting a web portion (101) off the web (100); and accelerating the web portion (101) to the speed (V2) of a receiving web (200), separating the web portion (101) into at least a first web portion (102) and a second web portion (103) by means of at least a second cut; moving the web portions (102, 103) relative to each other so that they are spaced apart; and applying each of the spaced apart web portions (102, 103) to the receiving web (200).

7 Claims, 2 Drawing Sheets

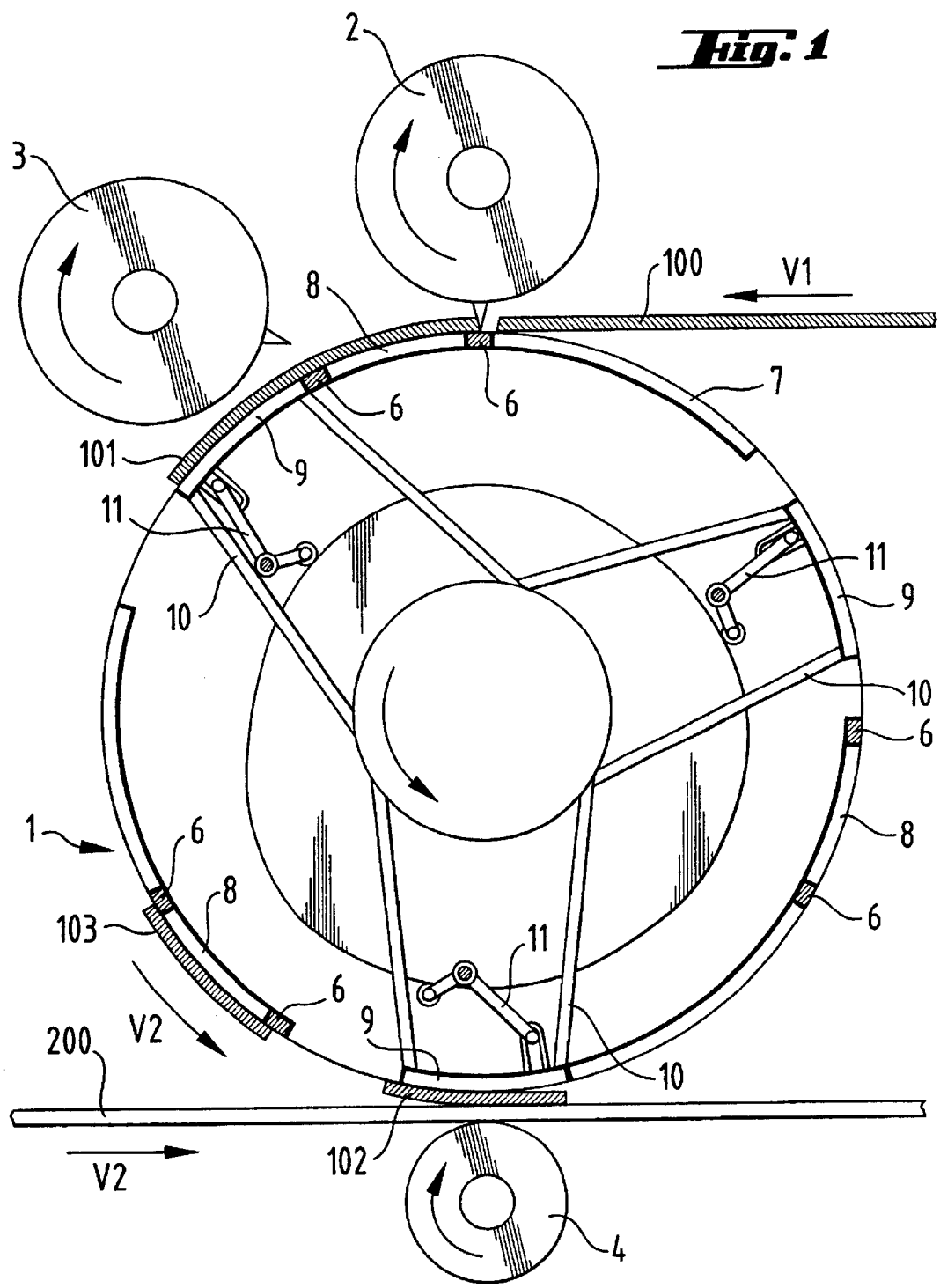

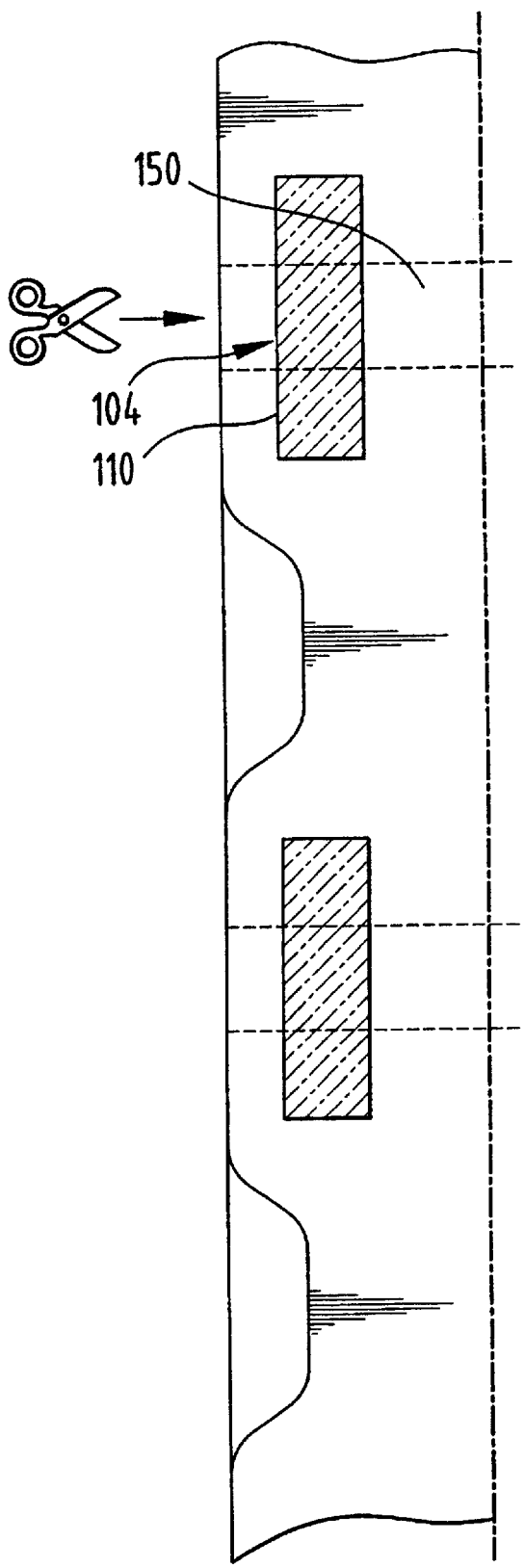
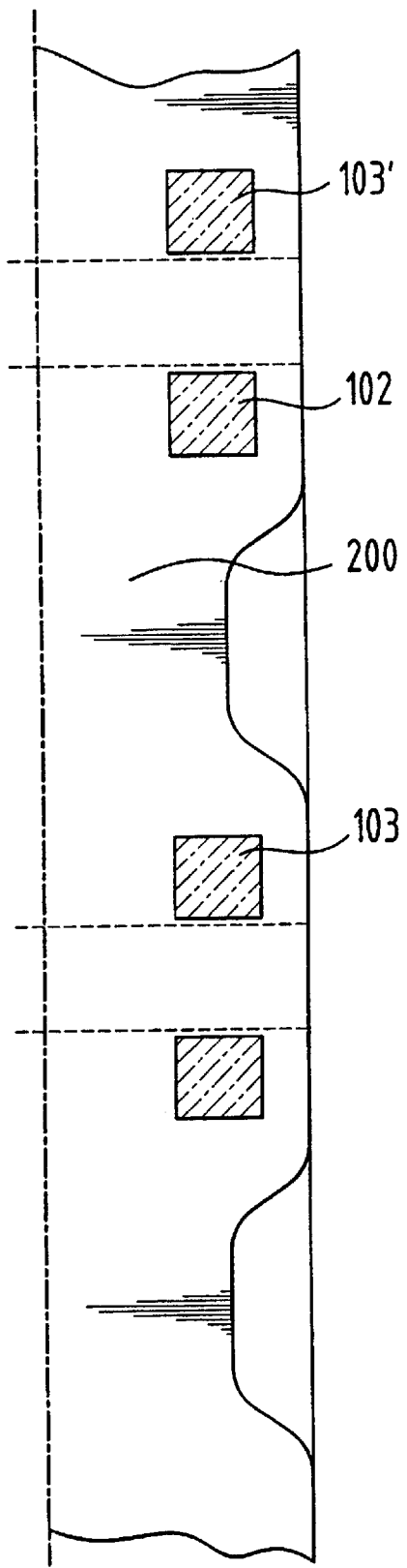

PROCESS FOR APPLYING DISCRETE WEB PORTIONS TO A RECEIVING WEB

The present invention relates to a process for applying discrete web portions, such as tapes or tape attachment zones or elastic bands, on to a receiving web, such as a diaper. In particular the process is applicable to high speed production lines used in the manufacture of diapers and similar products.

Diapers, adult incontinence products and the like, are usually manufactured on high speed production machines. Such machines generally form a continuous web which is transported through the machine in the machine direction in order to pass through a series of work stations. At each work station an operation is carried out. One common operation is to attach features such as tapes or tape attachment zones or elastic bands, on to a receiving web. Such features are often required to be discrete "patches", rather than continuous features which lie along the whole length (in the machine direction) of the receiving web. Such patches may be applied by various known techniques, including the technique known as "cut and slip".

An example of a known process is to provide an apparatus which receives discrete parts traveling at a first speed and applies them to a receiving web traveling at a second (usually faster) speed.

U.S. Pat. No. 5,660,657, issued on Aug. 26, 1997, illustrates an apparatus of this type in FIGS. 32 and 33. In the illustrated apparatus a rotating transfer assembly receives and holds the discrete parts, and transfers them to the receiving web.

Furthermore this patent discloses an apparatus which receives a continuous web traveling at a first speed, the web being cut into discrete parts and then applied to a receiving web traveling at a second (usually faster) speed. The end product has discrete parts which are spaced uniformly along the receiving web. FIGS. 35 and 36 of U.S. Pat. No. 5,660,657 illustrate such an apparatus. In the illustrated apparatus three rotating transfer assemblies receive and hold the discrete parts and transfer them to the receiving web. Each transfer assembly is mounted on an independently rotating shaft having a variable angular velocity.

Hence it is known to have a process with the steps of: feeding a web into a web transfer apparatus at a first speed; cutting a web portion off the web; and accelerating the web to the speed of a receiving web. This prior art process results is a receiving web upon which discrete parts are uniformly spaced.

However, in some cases, it would be advantageous to provide a receiving web upon which discrete parts are unevenly spaced. For example the spacing between a first and second, adjacent, discrete parts might be a distance X, whist the spacing between the second and third, adjacent, discrete parts might be a distance Y. Subsequently, the spacing between the third and fourth, adjacent, discrete parts might be the distance X again; the spacing between the fourth and fifth, adjacent, discrete parts might be Y again, and so on.

Furthermore, in some cases, it would be advantageous to provide discrete parts on to a receiving web whereby adjacent discrete parts are of unequal length (length being measured in the machine direction).

The object of the present invention is to provide a process which would provide a receiving web upon which discrete parts are either unevenly spaced, or which are unequal in length, or both, and which could be easily adjusted to provide different spacings between the discrete parts, and/or different lengths of discrete parts, so that different products, or different sizes of products, can easily be manufactured on the same apparatus.

SUMMARY OF THE INVENTION

This object is achieved by: separating the web portion into at least a first web portion and a second web portion by means of at least a second cut; moving the web portions relative to each other so that they are spaced apart; and applying each of the spaced apart web portions to the receiving web.

BRIEF DESCRIPTION OF THE DRAWINGS

FIG. 1 shows a schematic side-view of an apparatus suitable for carrying out the process of the present invention.

FIG. 2A shows the left-hand half of a continuous web of prior art diapers, prior to being cut into individual diapers.

FIG. 2B shows the right-hand half of a continuous web of diapers made according to the process of the present invention, prior to being cut into individual diapers.

DETAILED DESCRIPTION OF THE INVENTION

It will be readily apparent to those skilled in the art that although the following description of the present invention is in connection with a single use diaper structure having web portions such as discrete elastic regions or strips applied thereto, the present invention may be practiced with equal facility on nearly any web.

In the following description a "receiving web" is a web of material which is continuous in the machine direction. A preferred receiving web comprises a plurality of interconnected single use disposable absorbent articles, such as diapers. Typically, each diaper is comprised of an absorbent pad element or absorbent core, and web portions such as elastomeric elements or patches. The absorbent pad elements and the elastomeric elements are located between a backsheet and a topsheet, or alternatively, on top of a backsheet or topsheet. The continuous webs of backsheet material and topsheet material are preferably maintained under very slight tension in the machine direction to prevent wrinkling and to facilitate registration with the diaper assembly and converting operations until the completed diaper web is severed into discrete diapers by cutting across the width of the web. The term "diaper" is used herein to refer to diapers for babies or infants, to refer to training pants, and also to refer to adult incontinence products.

In a first embodiment of the present invention the receiving web is cut into discrete lengths (e.g. individual diapers) by cutting across the width of the receiving web after applying each of the spaced apart web portions to the receiving web, and each discrete length of the receiving web has at least the first web portion and the second web portion applied to it.

It is desirable, in some cases, to provide web patches which are symmetrically applied on either side of a machine direction axis of the receiving web, such as the centre line of the receiving web (e.g. left side panels and right side panels, or, in the case of a diaper, left leg elastic cuffs and right leg elastic cuffs). This can be achieved by providing a further cut along a line orthogonal to the second cut, in order to provide a first left-side web portion; a first right-side web portion; a second left-side web portion; and a second right-side web portion, the web portions being applied so as to be substantially symmetrical on either side of a machine direction axis of the receiving web.

In this first embodiment of the invention the length of each individual diaper defines a certain pitch (i.e. the length of the individual diaper in the machine direction). When it is desired to apply one web portion per pitch to the receiving web, then the prior art processes (e.g. "cut and slip") are adequate to achieve this. However, when it is desired to apply two, or more than two, web portions per pitch, and when adjacent web portions within one pitch are required to be close together, then the prior art processes are unsuitable. The prior art processes are only suitable to provide one web portion per pitch (or possibly evenly spaced multiples of web portions per pitch).

In second embodiment of the invention, the length in the machine direction of the first web portion, and the length in the machine direction of the second web portion, is unequal. The first and second embodiments of the invention may be combined.

FIG. 1 illustrates schematically an example of the process of the present invention. An incoming web 100 is fed with a velocity V1 between a first knife roll 2 and a first anvil 6, to make a first cut, and web portion 101 which has been cut from the incoming web 100 is held by vacuum shoes 8 and 9. The web portion 101 corresponds in length to the total length of the first and second tapes 102, 103. The web portion 101 is held on the web transfer apparatus 1 which accelerates the web portion to match the velocity V2 of the receiving web 200. In the next step a second cut is made between a second knife roll 3 and a second anvil 6 to separate the web portion 101 into a first tape 102 and a second tape 103. The first tape 102 is held by a vacuum shell 9, which, in turn is supported by an oscillating arm 10. The oscillating arms 10 (of which three are illustrated in FIG. 1) are mounted independently on the main shaft of the web transfer apparatus 1. The first tape 102 is subsequently advanced relative to the second tape 103 by means of a cam mechanism 11 connected to the vacuum shell/oscillating arm assembly, 9, 10, so that the first and second tapes are spaced apart by a distance corresponding to the distance between the first and second tapes required in the finished diaper. Finally the first and second tapes are applied to the receiving web 200 at matched speeds by means of a transfer roll 4. A similar series of process steps is used to apply the first and second tape landing patches.

In a particular aspect of the present invention, the receiving web 200 has a series of web portions applied to it, each web portion being cut into at least a first web portion 102 and a second web portion 103, and wherein the distance between any web portion 102 and the two web portions on either side of it 103, 103' in the machine direction, is unequal. For example, FIG. 2B illustrates a diaper 200 having tapes 102 and tape landing patches 103 affixed to the backsheet of the diaper 200. The tapes 102 are used to fasten the diaper 200 around the waist of the wearer and they are secured by releasable attachment to the tape landing patches 202. In FIG. 2B the tapes will be referred to as a first tape 101 and a second tape 32, and the tape landing patches as a first tape landing patch 31, and a second tape landing patch 32.

FIG. 2A shows a prior art diaper in which the web portions 104 are applied in strips 110 which overlap the waist region 150 of both of two adjoining diapers. This limits product design because the waist region 150 must accommodate the material of the web portion 150. When a waist elastic is subsequently laid in the waist region 150, the waist elastic overlays the web patch 104.

Of course the process of the present invention can be easily adapted to provide more than two web portions per diaper. In case three web portions are provided, then a second and third cut separates the web portion into three parts (a first web portion, second web portion and third web portion), and two of these web portions are then accelerated in order to move the web portions apart by the required spacing.

What is claimed is:

1. A process comprising the steps of:
   feeding a web into a web transfer apparatus (1) at a first speed (V1);
   cutting a web portion (101) off the web (100); and
   accelerating the web portion (101) to the speed (V2) of a receiving web (200),
   characterised in that the process further comprises the steps of:
   separating the web portion (101) into at least a first web portion (102) and a second web portion (103) by means of at least a second cut;
   moving the web portions (102, 103) relative to each other so that they are spaced apart;
   and applying each of the spaced apart web portions (102, 103) to the receiving web (200).

2. A process according to claim 1 wherein the receiving web (200) is cut into discrete lengths after applying each of the spaced apart web portions (102, 103) to the receiving web (200), and wherein each discrete length of the receiving web has at least the first web portion (102) and the second web portion (103) applied to it.

3. A process according to claim 2 wherein each of the first and second web portions (102, 103) are further cut along a line orthogonal to the second cut, in order to provide a first left-side web portion; a first right-side web portion; a second left-side web portion; and a second right-side web portion, the web portions being applied so as to be substantially symmetrical on either side of a machine direction axis of the receiving web (200).

4. A process according to claim 2 wherein the discrete length of the receiving web (200) is a diaper, training pant or adult incontinence product which further comprises a topsheet, a backsheet and an absorbent core.

5. A process according to claim 4 wherein the web portion (102, 103) is a tape or tape attachment zone or elastic band.

6. A process according to claim 1 wherein the receiving web (200) has a series of web portions (101) applied to it, each web portion being cut into at least a first web portion (102) and a second web portion (103), and wherein the distance between any web portion (102) and the two web portions on either side of it (103, 103') in the machine direction, is unequal.

7. A process according to claim 1 wherein the length in the machine direction of the first web portion (102), and the length in the machine direction of the second web portion (103), is unequal.

* * * * *